(12) United States Patent
Ueda

(10) Patent No.: US 8,951,765 B2
(45) Date of Patent: Feb. 10, 2015

(54) TARGETED SEPARATION OF CULTURED CELLS

(75) Inventor: Masahiro Ueda, Kyoto (JP)

(73) Assignee: Empire Technology Development LLC, Wilmington, DE (US)

( * ) Notice: Subject to any disclaimer, the term of this patent is extended or adjusted under 35 U.S.C. 154(b) by 1082 days.

(21) Appl. No.: 12/624,972

(22) Filed: Nov. 24, 2009

(65) Prior Publication Data

US 2011/0124076 A1    May 26, 2011

(51) Int. Cl.
*C12N 13/00* (2006.01)
*C12M 1/00* (2006.01)

(52) U.S. Cl.
CPC ............... *C12M 47/04* (2013.01); *C12M 47/02* (2013.01)
USPC ............ 435/173.9; 435/261; 435/288.4; 435/288.5; 435/308.1; 435/325

(58) Field of Classification Search
None
See application file for complete search history.

(56) References Cited

U.S. PATENT DOCUMENTS

| 7,169,577 | B2* | 1/2007 | Wang et al. ............... | 435/30 |
| 2003/0219889 | A1 | 11/2003 | Sumaru et al. | |
| 2004/0234954 | A1* | 11/2004 | Nusslein et al. ............ | 435/5 |
| 2007/0026413 | A1* | 2/2007 | Toner et al. ................. | 435/6 |

FOREIGN PATENT DOCUMENTS

| WO | 2005/060668 | 7/2005 |
| WO | 2006/133208 | 12/2006 |

OTHER PUBLICATIONS

Elder, GA et al. Schwann cells and oligodendrocytes read distinct signals in establishing myelin sheath thickness. Journal of Neuroscience Research. 2001. 65: 493-499.*
Ichimura, K et al. Light-driven motion of liquids on a photoresponsive surface. Science. Jun. 2, 2000. 288: 1624-1626.*
Hayden, O et al. Biomimetic ABO blood-group typing. Angew. Chem. Int. Ed. 2006. 45: 2626-2629.*
Sasaki, YC et al. Observation of nanometer-level structural changes by the trans-cis transition of an azobenzene derivative monolayer with a radioactive tracer. Langmuir. 1996. 12: 4173-4175.*
Huaiqiu Shi, et al "Template-imprinted nanostructured surfaces for protein recognition" Nature, vol. 398, Apr. 15, 1999, pp. 593-597.
Kahp Y. Suh, et al "A simple soft lithographic route to fabrication of poly(ethylene glycol) microstructures for protein and cell patterning" Biomaterials, vol. 25, 2004, pp. 557-563.
Varian "SPS3 autosampler from Varian, Inc." Online: http://www.varianinc.com/image/vimage/docs/products/spectr/general/accessories/si-0249.pdf, 4 pages. May 2008.
Beckman "VI-Cell AS (Autosampler) Complete System" Online: http://www.beckman.com/eCatalog/CatalogItemDetails.do?productId=13068, 2 pages. Accessed Aug. 24, 2009.
Dino Di Carlo, et al "Dynamic single cell culture array" Lab on a Chip, vol. 6, 2006, pp. 1445-1449.
Makoto Hasegawa, et al "Topographical Nanostructure Patterning on the Surface of a Thin Film of Polyurethane Containing Azobenzene Moity Using the Optical Near Field around Polystyrene Spheres" Macromolecules, vol. 34, No. 21, 2001, pp. 7471-7476.
Osamu Watanabe, et al "Two-step refractive index changes by phtoisomerization and photobleaching process in the films of non-linear optical polyurethanes and a urethane-urea copolymer" J. Mater. Chem., 1996, 6(9), pp. 1487-1492.
Joel Voldman "Biomems: Building with Cells" Nature Materials, vol. 2, Jul. 2003, pp. 433-434.
Takaaki Suzuki, et al "High Throughput Electroporation Microchip Fabricated by Single-mask Inclined UV Lithography" The 12th International Conference on Miniaturized Systems for Chemistry and Life Sciences [MicroTAS2008], pp. 1519-1521, Oct. 12-16, 2008, San Diego, USA.
Jamil El-Ali, et al "Cells on Chips" Nature, vol. 442, Jul. 27, 2006; pp. 403-411.
T. Suzuki, et al "Simple Fabrication Process for Single Cell Analysis Chip Composed of Embedded Microchannels and Orifices" The 2nd International Symposium on Micro & Nano Technology (ISMNT-2), Hsinchu, Taiwan, pp. 222-225, 2006.
Yan-Jun Liu, et al "A micropillar-integrated smart microfluidic device for specific capture and sorting of cells" Electrophoresis 2007, 28, pp. 4713-4722.
Joseph A. Phillips, et al "Enrichment of cancer cells using aptamers immobilized on a microfluidic channel" Analytical Chemistry, 81(3), 1033-1039, Feb. 1, 2009.
Kazunori Kataoka, "Molecular design of materials for cell separation" Artificial Organs, vol. 12, Issue 6, Dec. 1988, pp. 511-513—$35.
P. Gorostiza et al "Optical switches for remote and noninvasive control of cell signaling" Science, 2008, vol. 322, No. 5900, p. 395-399.
Almeria Natansohn, et al "Photoinduced motions in Azo-Containing Polymers", Chemical Reviews, 2002, vol. 102, No. 11, pp. 4139-4175.
Jun-ichi Edahiro, et al "In Situ Control of Cell Adhesion Using Photoresponsive Culture Surface" Biomacromolecules, 2005, 6 (2), pp. 970-974.
Australian Patent Office; International Search Report and Written Opinion in corresponding PCT application (PCT/US2010/057749); mailed Mar. 29, 2011.

* cited by examiner

*Primary Examiner* — Allison Fox
*Assistant Examiner* — Susan E Fernandez
(74) *Attorney, Agent, or Firm* — Dorsey & Whitney LLP

(57) ABSTRACT

Embodiments described herein relate to separating and/or concentrating target cells from a carrier fluid that may include other non-target cells. Embodiments include a cell separator with a flow surface having indentations formed thereon. The indentations are configured to capture target cells by physical and/or chemical interactions. The indentations may also include a layer of support molecules that assist in releasing captured cells for collection.

14 Claims, 8 Drawing Sheets

TARGETED SEPARATION OF CULTURED CELLS

TECHNICAL FIELD

Embodiments described herein can broadly be used in technical fields implicating cell culturing systems to facilitate culturing and harvesting of cells.

BACKGROUND

Generally, cells are cultured in vitro in either suspended cultures or adherent cultures. In suspended culture, cultured cells are grown while suspended in a growth media. Cell cultures grown in suspension are typically derived from cell types that naturally live in suspension without being attached to a surface or to one another. In adherent cell culture environments, cultured cells adhere to surfaces (e.g., the surfaces of a culture vessel) and/or to one another as a support for cell growth.

Examples of suspended cells that can be cultured in vitro include blood cells, lymphocyte cells, and the like. Examples of adherent cells that can be cultured in vitro include epithelial cells, hematopoietic cells, mast cells, neurocytes, hepatocytes, hepatic parenchymal cells, bone marrow cells, osteoblasts, fibroblasts, epidermal cells, many stem cell types, and the like.

When adherent cells are ready for harvesting, chemical means such as enzymes (e.g., collagenase) and/or physical means such as glass capillary colony cutters have generally been used to separate the cells from the growth surface and/or to separate the cells from one another. Harvesting of cells grown in suspension or suspended adherent cells is typically performed by filtration, centrifugation, antibody processes, beads, pipetting, and the like. However use of chemicals, enzymes, and/or physical means to separate cultured cells can damage the cells.

In some cases, different types of cells are mixed in culture. For example, stem cells may be cultured with feeder cells, or stimulating cells (e.g., antigen presenting cells and a cancer cell line) may be co-cultured. In cases where mixed cultures are concerned, separation of the cells in the mixed culture can be additionally complicated and require additional physical and/or chemical processes, such as filtration, centrifugation, antibody, or beads. Again, these processes can damage the cells.

SUMMARY

In one embodiment, the present disclosure describes an apparatus for cell separation. In one aspect, the apparatus includes a channel having an inlet and an outlet, the inlet configured to receive an initial carrier fluid containing at least a first cell, and a flow surface extending between the inlet and the outlet of the channel, wherein the flow surface is configured to selectively capture at least the first cell and to permit the carrier fluid flow therethrough.

In another embodiment, the present disclosure describes an apparatus for separating or concentrating target cells. In one aspect, the apparatus may include a channel having an inlet and an outlet, the inlet configured to receive an initial carrier fluid containing a plurality of first target cells, and a flow surface extending between the inlet and the outlet of the channel, the flow surface configured to include one or more indentations configured to capture one or more of the plurality of first target cells when the initial carrier fluid passes over the flow surface, leaving extraneous carrier fluid to flow to the outlet of the channel.

In yet another embodiment, the present disclosure describes a method for separating target cells from a carrier fluid. In one aspect, the method may include passing an initial carrier fluid containing a plurality of first target cells through an inlet of a channel to pass over a flow surface of the channel, the flow surface having at least one indentation sized with a diameter that substantially matches a diameter of at least a portion of the first target cell to capture one or more of the plurality of first target cells as the initial carrier fluid passes over the flow surface, leaving extraneous carrier fluid to flow to an outlet of the channel, and applying a first energy source to initiate release of the captured one or more target cells from the at least one indentation such that the released one or more target cells flow to the outlet of the channel.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION

Figure 1A:
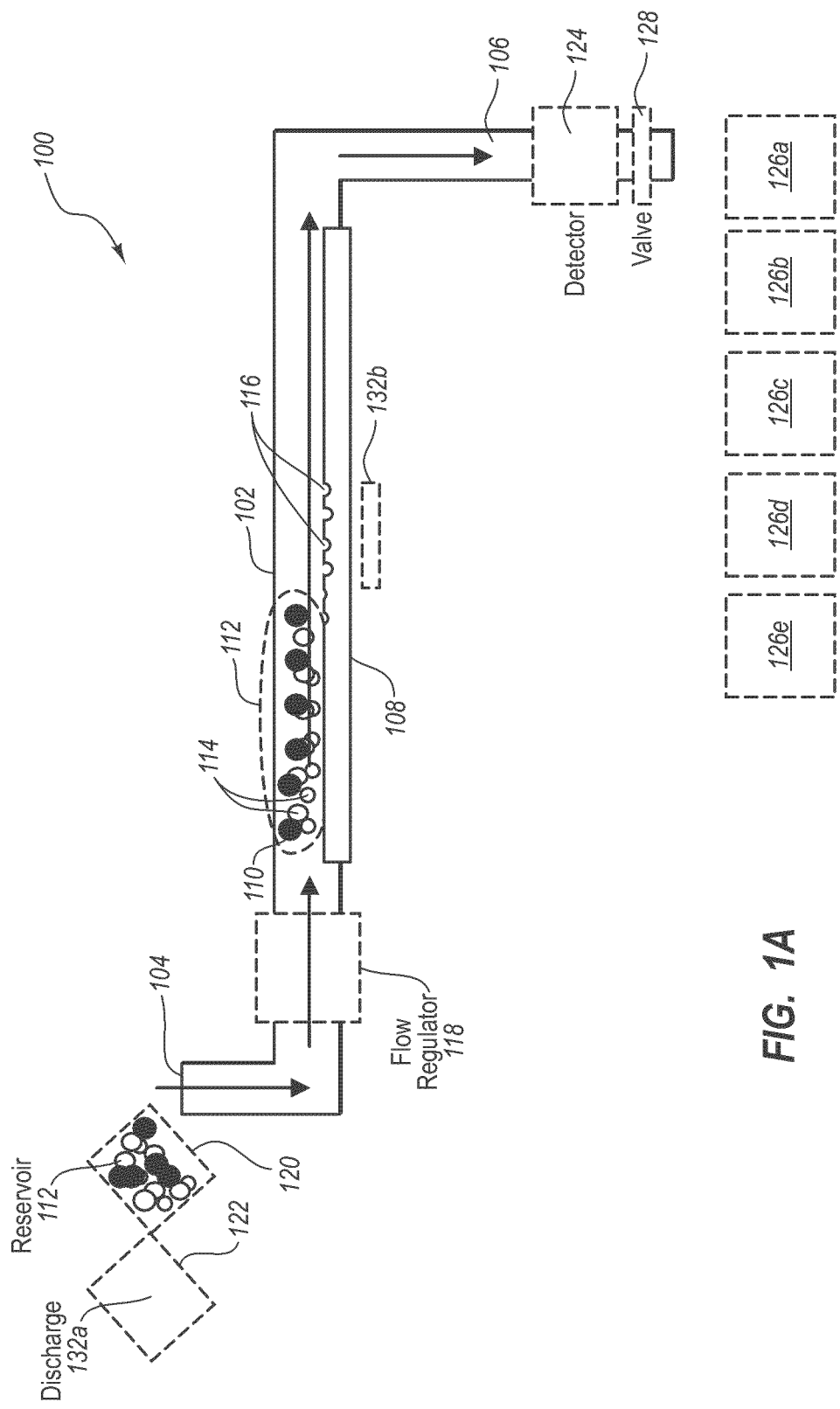
FIG. 1A is a schematic diagram of an illustrative embodiment of a cell separator, in a first stage of operation.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Introduction

Embodiments herein are directed to separation (e.g., harvesting) of cultured cells without damaging the cells. Embodiments described herein provide compositions, apparatuses, and methods for culturing and harvesting cells without use of conventional chemical and physical harvesting methods. Cells are suspended in a carrier fluid from which it is desired to separate one or more target cells and, optionally, from other non-target cells contained in the carrier fluid. In one aspect, this may be accomplished by providing an apparatus that can selectively capture then subsequently release cells while allowing the carrier fluid to flow through the apparatus.

The carrier fluid can be, in one embodiment, a culture medium in which cultured cells were suspended to mature, such as, but not limited to saline, bovine serum, fetal calf serum, Dulbecco's modified Eagle's medium (DMEM), nutrient broths, and the like. The carrier fluid can include any combination of adherent cells, floating cells, feeder cells, stimulating cells, and the like. Alternatively, the carrier fluid may have only target cells carried therein, in which it is desired to concentrate or separate the target cells from the carrier fluid. In any case, the term "target cell" will be used to refer to a particular type of cell or aggregation of cells that is desired to be separated from the rest of the carrier fluid and/or non-target cells.

Various types of adherent cells can be cultured including, but not limited to, stem cells, osteocyte, epidermal cells, organ cells (e.g., blood vein cells, vascular cells, liver cells (i.e., hepatocytes), cardiac cells, etc), or other tissue engineering cells, and the like. Additional examples of adherent cells include, but are not limited to, epithelial cells, ciliated epithelial cell, chondrocyte (e.g., fibrocartilage, elastic cartilage), osteoblasts, osteocytes, muscle cells (e.g., smooth muscle cells, skeletal muscle cells, myocardial cells), neurocytes (e.g., glia cells, schwan cells, myelin sheath cells), hematopoietic cells, mast cells, hepatocytes, hepatic parenchymal cells, and bone marrow cells. Examples of stem cells include, but are not limited to, embryonic stem cells (ESCs), pluripotent stem cells, induced pluripotent stem cells, embryonic stem cells, adult stem cells, and multipotent and induced multipotent stem cells such as neural cells, mesencymal stem cells, epithelial stem cells, bone marrow stem cells, neural stem cells, hematopoietic stem cells, germ stem cells, somatic stem cells, modified stem cells, and the like. Examples of mammalian cells that can be cultured in suspension (i.e., floating cells) include, but are not limited to cells that are present in the blood stream. Cells that are present in the blood stream include, but are not limited to, granulocytes (e.g., neutrophils, eosinophils, basophils), lymphocytes (e.g., B lymphocytes, T lymphocytes, NK (natural killer) cells), monocyte, and the like. Many non-mammalian cells have also been adapted for growth in suspension. For example, cells isolated from ovarian tissue of the fall army worm, *Spodoptera frugiperda*, and from embryonic tissue from the *Trichoplusia ni* have been adapted for growth in suspension and they are used in many laboratories. Many microorganisms are also adapted for growth in suspension. For example, many species of bacteria (e.g., *E. Coli, S. aureus, S. typhimurium*, etc), archea (e.g., *Sulfolobus solfataricus, halobacteria* (e.g., *Halobacterium salinarum*)), protists (e.g., algae, dinoflagellates, and euglena), and fungi (e.g., baker's yeast (*Saccharomyces cerevisiae*) and fission yeast (*Schizosaccharomyces pombe*)) are adapted for growth in suspended culture.

One example of cells that are commonly co-cultured include stem cells and feeder cells. A feeder cell is generally a non-dividing cell that is co-cultured with a multiplying cell type (e.g., a stem cell) for the purpose of providing necessary growth factors, nutrients, and other co-factors to the dividing cells. Suitable examples of feeder cells include, but are not limited to, mouse embryonic fibroblast cells, mouse liver cells, zenogenetic feeder cells, allogenetic feeder cells, allogenetic fibroblast cells, artificial feeder cells, and combinations thereof. Another example of cells that are commonly co-cultured are stimulating cells. For example, for stimulation a Mixed Lymphoid Reaction (MLR) is commonly done (e.g., T-lymphocytes and dendritic cells plus antigen, or T-lymphocytes and a cancer cell line).

Embodiments thus provide compositions, apparatuses, and methods for separation of cultured cells. One aspect includes a cell separator having a channel with an inlet and an outlet. The channel has a flow surface extending between the inlet and the outlet. The channel can have any of various shapes including being a closed channel in which a wall substantially surrounds the channel from the inlet to the outlet. Or, the channel could have an open top. The channel can have any of various cross sections including, but not limited to, circular, elliptical, square, triangular, or other polygonal shape, or any partial polygonal shape, and the like. The channel can be substantially straight, or have a curved portion. The channel could be substantially horizontal, or could rest at an incline. Basically, the channel can have various configurations that will be apparent to one of skill in the art.

The flow surface separates target cells from an initial carrier fluid and/or other non-target cells in the initial carrier fluid when the initial carrier fluid passes over the flow surface. The flow surface may be configured to selectively capture at least a first cell and to permit the carrier fluid to flow therethrough. For example, the flow surface may be configured to include indentations sized and configured for selectively capturing target cells from the initial carrier fluid when the carrier fluid passes over the flow surface. In one aspect, the indentations can be sized with a diameter substantially similar to at least a portion of a target cell such that the target cells can fit into the indentations and be captured thereby. In another aspect, the indentations can be sized with a diameter sufficient to encompass $1/8$, $1/5$, $1/4$, $1/3$, or $1/2$ of the mass of the target cells at least a portion of the target cells can fit into the indentations and be captured thereby. The inlet of the channel is configured to receive an initial carrier fluid containing target cells. In one embodiment, the indentations on the flow surface capture target cells when the initial carrier fluid passes over the flow surface, leaving extraneous carrier fluid to flow to the outlet of the channel.

In one embodiment, the flow surface can be configured to release the cells subsequent to their have been selectively captured. For example, the indentations may be configured to release the captured target cells responsive to a first energy source to allow the released target cells to flow to the outlet of the channel. For example, the indentations can be formed from a material having a photo-responsive region configured to change conformation and/or chemical state in response to exposure to the first energy source. In one aspect, the indentations can be configured to change conformation between at least a more hydrophobic state and more hydrophilic state in response to exposure to the first energy source. When the indentations are in a more hydrophobic state, the indentations have a first conformation that is more accessible and/or suitable for association with and optionally adherance by cultured cells. In contrast, when the indentations have a more hydrophilic state, the indentations have a second conformation that is less accessible and/or less conducive to association with and optionally adherance by cultured cells. In one embodiment, the first energy source is applied at a particular time that causes the released target cells to flow to the outlet of the channel at a delayed period after the extraneous carrier fluid flows to the outlet of the channel.

Any combination of target cells and/or non-target cells may be contained in the initial carrier fluid. When the initial carrier fluid includes non-target cells along with target cells, the non-target cells pass over the flow surface with the extraneous carrier fluid. The non-target cells can be collected separately from the target cells. In one embodiment, the first energy source is applied at a particular time that causes the released target cells to flow to the outlet of the channel at a delayed period after the non-target cells flow to the outlet of the channel.

The apparatus can further include a detector in communication with the outlet of the channel that detects flow of extraneous carrier fluid flowing from the outlet of the channel and/or flow of the released target cells flowing from the outlet of the channel. The apparatus can include a flow regulator in fluid communication with the inlet of the channel that regulates a flow of the initial carrier fluid and/or a flow of discharge fluid into the inlet of the channel. In one embodiment, the discharge fluid is configured to provide a first energy source to release the captured target cells from the indentations. In one embodiment, the discharge fluid is applied at a particular time that causes the released target cells to flow to the outlet of the channel at a delayed period after the extraneous carrier fluid. In another embodiment, a stimulus, such as an optical device, provides the first energy source to release the captured target cells from the indentations. The apparatus can include a reservoir connected to the flow regulator and configured to hold initial carrier fluid and/or discharge fluid.

One aspect includes a method that includes passing an initial carrier fluid containing target cells through an inlet of a channel to pass over a flow surface of the channel. In one aspect, the flow surface has indentations sized with a diameter that substantially matches a diameter of the target cells such that the target cells can fit into the indentations and be captured thereby. In another aspect, the indentations can be sized with a diameter sufficient to encompass ⅛, ⅕, ¼, ⅓, or ½ of the mass of the target cells at least a portion of the target cells can fit into the indentations and be captured thereby. The indentations on the flow surface capture target cells as the initial carrier fluid passes over the flow surface, leaving extraneous carrier fluid to flow to the outlet of the channel. A first energy source is applied to initiate release of the captured target cells from the indentations such that the released target cells flow to the outlet of the channel. In one embodiment, the first energy source is applied at a particular time that causes the released target cells to flow to the outlet of the channel at a delayed period after the extraneous carrier fluid flows to the outlet of the channel. In one embodiment, the first energy source is a discharge fluid being applied to the inlet of the channel. In another embodiment, the first energy source is a stimuli, such as an optical device, being applied to the flow surface.

The flow surface of the channel can include a substrate that is made from various non-corrosive and bio-safe materials including, but not limited to, glass, quartz, polycarbonate, plastic, silicon, aluminum, stainless steel, ceramic, and the like. Other materials for making the substrate will be readily apparent to those skilled in the art, thus further description will not be provided to avoid obscuring the concepts herein.

The indentations in the flow surface can be made using various polymer techniques, soft lithography techniques, BioMEMS techniques, µTAS techniques, and the like. In one embodiment, the process of making indentations results in the indentations including a functional group configured to interact with target cells having complementary functional groups. In another embodiment, the indentations can be formed being at least partially coated with support molecules having a first region configured to bind to a surface of the indentation and a photo-responsive region configured to change conformation between a first conformation and a second conformation responsive to irradiation from an optical energy source. The use of the term "support molecule" simply refers to molecules that modify the indentations to enhance the ability of the indentations to interact with and/or release the target cells. The term "support" when used in reference to molecules is not intended to refer to any particular structure or characteristic of the molecules themselves.

In view of the foregoing, apparatuses for targeted separation of cultured cells, methods for targeted separation, and methods for manufacturing flow surfaces having indentations for use in targeting separation of cells will now be described in further detail with reference to the drawings.

Illustrative Embodiments for Cell Separator Apparatus

FIG. 1A is a schematic diagram of an illustrative embodiment of a cell separator 100. Cell separator 100 includes a channel 102 with an inlet 104 and an outlet 106. The channel 102 has a flow surface 108 extending between the inlet 104 and the outlet 106. The channel 102 can have any of various shapes including being a closed channel (shown in FIG. 1A) in which a wall substantially surrounds the channel from the inlet 104 to the outlet 106. Or, the channel 102 could have an open top. The channel 102 can have any of various cross sections including, but not limited to, circular, elliptical, square, triangular, or other polygonal shapes. Furthermore, when the channel 102 has an open top, the cross section can be a partial circle, partially elliptical, partially square, partially triangular, or other partial polygonal shapes. The channel 102 can be substantially straight (shown in FIG. 1A), or have a curved portion. The channel 102 could be substantially horizontal (shown in FIG. 1A), or could rest at an incline. Illustrative dimensions for the channel 102 include a length of about 5 cm to about 50 cm, or about 5 cm to about 30 cm, or about 5 cm to about 15 cm, with a diameter of about 0.1 cm to about 1 cm, or about 0.3 cm to about 1 cm, or about 0.5 cm to about 1 cm. Basically, the channel 102 can have any of various configurations, so the shape of the channel will not be discussed in further detail to avoid obscuring the concepts herein.

The flow surface 108 separates target cells 110 from an initial carrier fluid 112 (shown by the dashed line) and/or other non-target cells 114 contained in the initial carrier fluid 112 when the initial carrier fluid 112 passes over the flow surface 108. The flow surface 108 is configured to include indentations 116 sized with a diameter substantially similar to but not smaller than at least a portion of a target cell 110. The flow surface 108 can have an area of any shape and usually conforms to the cross-section of the channel 102. The flow surface 108 could cover the entire channel 102, or only a portion of the channel 102. Illustrative dimension of an area of the flow surface 108 can be about 0.1-1 cm by about 3-30 cm square. Illustrative sizes for the indentations will be described further below. Basically, the size and shape of the surface area of flow surface 108 can have any of various configurations, so will not be discussed in further detail to avoid obscuring the concepts herein.

Optionally, the apparatus 100 can include a flow regulator 118 that is in fluid communication with the inlet 104 of the channel 102. The flow regulator 118 regulates a flow of the initial carrier fluid 112 from a first reservoir 120 (optional) that is connected to the flow regulator 118 and holds initial carrier fluid 112. The flow regulator 118 may also be connected to a second reservoir 122 (optional) that holds discharge fluid 132a that can flow into the inlet 104 of the channel 102. In one embodiment, the flow regulator 118 can operate the flow of from the first reservoir 120 at a different flow rate than the flow from the second reservoir 122. In one embodiment, the flow regulator 118 is a pump such as, but not limited to a peristaltic pump, diaphragm pump, and the like. In one embodiment, the flow regulator 118 operates at a flow rate ranging from about 0.5 mm$^3$/min to about 200 cm$^3$/min, or about 1 mm$^3$/min to about 10 cm$^3$/min, or about 10 mm$^3$/ min to about 1 cm³/min, or about 100 mm³/min to about 1 cm³/min, as illustrative examples. Various types of flow regulators are commercially available. Example flow regulators include, but are not limited to, ultrasonic flowmeter (Transonic Systems Inc., Ithaca, N.Y.), electlomagnetic blood flowmeter (NIHON KOHDEN CORPORATION, Tokyo, Japan) liquid flow meter ASL1600 (Sensirion AG, Zurich). The flow meter can also include a separate flow pump and a flow meter for achieving flow control.

In one embodiment, the first reservoir 120 and second reservoir 122 may be the same device and may hold target cells and/or non-target cells separately from the carrier fluid. In one embodiment, the carrier fluid is used to carry the target cells and/or non-target cells through the channel 102 and also serves as the discharge fluid. In other embodiments, a separate liquid is used as the discharge fluid. Examples of carrier fluids include, but are not limited to saline, bovine serum, fetal calf serum, Dulbecco's modified Eagle's media, nutrient broths, and the like. Examples of discharge fluids include, but are not limited to, saline, bovine serum, fetal calf serum, Dulbecco's modified Eagle's media, nutrient broths, and the like.

Optionally, the apparatus 100 can further include a detector 124 in communication with the outlet 106 of the channel 102 that detects flow of carrier fluid, discharge fluid, target cells, and/or non-target cells flowing from the outlet 106 of the channel 102. In one embodiment, the detector 124 is one of an optical density detector, an absorption spectrometer, or a turbidimeter. In another embodiment, the detector 124 is an autosampler that can both detect flow of carrier fluid, discharge fluid, target cells, and/or non-target cells flowing from the outlet as well as dispense cells into different sampling containers (described below). Examples of autosamplers are commercially manufactured and available by Varian Medical Systems and Beckman Coutler. Various types of detectors 124 are commercially available so will not be described in further detail to avoid obscuring the concepts herein.

Optionally, the apparatus 100 can also include one or more sampling containers 126a through 126e positioned near the outlet 106 of the channel 102. Suitable examples of sampling containers include, but are not limited to, culture dishes, test tubes, microcentrifuge tubes (e.g., Eppendorf tubes), conical centrifuge tubes, culture flasks, and the like. In one embodiment, the sampling containers 126a through 126e are configured to rotate positioning underneath the outlet 106 so that each sampling container 126 collects different materials flowing through the channel 102, as described further below.

When the detector 124 does not have an autosampling function, a flow regulating valve 128 can be installed below the detector 102. When detector 102 detects passage of the desired target cells, then regulating valve 128 can be closed, stopping fluid flow from the outlet 106 of the channel 102. A clean sampling container can be positioned under the outlet 106 and then the flow regulating valve 128 opened to collect the target cells. In this embodiment, preferably the detector 124 is placed along channel 102 at a location sufficient to allow the regulating valve 128 to close before the target cells reach an end of the outlet 106.

Finally, the apparatus 100 can optionally include a stimuli device 132b disposed in communication with the flow surface 108 to apply a stimulus to the flow surface 108, as described below in further detail.

Illustrative Operations for Separating Target Cells

FIGS. 1A through 1D are schematic drawings of the illustrative embodiment of the apparatus 100 in various stages of operation. In FIG. 1A, the reservoir 120 contains initial carrier fluid 112. To prepare the initial carrier fluid, target cells 110 and/or non-target cells 114 are selected from a culture in which it is desired to concentrate and/or separate the target cells 110. Adherent cells can be detached a culture dish using, for example, trypsin EDTA. The trypsin can be deactivated using an equal amount of Dubelcco's Modified Eagle's Medium and 10% fetal bovine se. Cells can then be centrifuged to a pellet and resuspended in phosphate buffered saline pH 7.4. The suspension forms the initial carrier fluid. The suspension can additionally include adhesion-promoting proteins that assist target cells to adhere to hydrophobic surfaces. Other methods for preparing initial carrier fluid are commercially known and available.

The regulator 118 can be operated to initiate a flow of initial carrier fluid 112 containing at least target cells 110 from the reservoir 120. The inlet 104 of the channel 102 receives the initial carrier fluid 112 containing target cells 110. Any combination of target cells 110 and/or non-target cells 114 may be contained in the initial carrier fluid 112. The initial carrier fluid 112 passes over the flow surface 108 of the channel 102. In one embodiment, the initial carrier fluid 112 has a combination of target cells 110 and non-target cells 114.

Figure 1B:
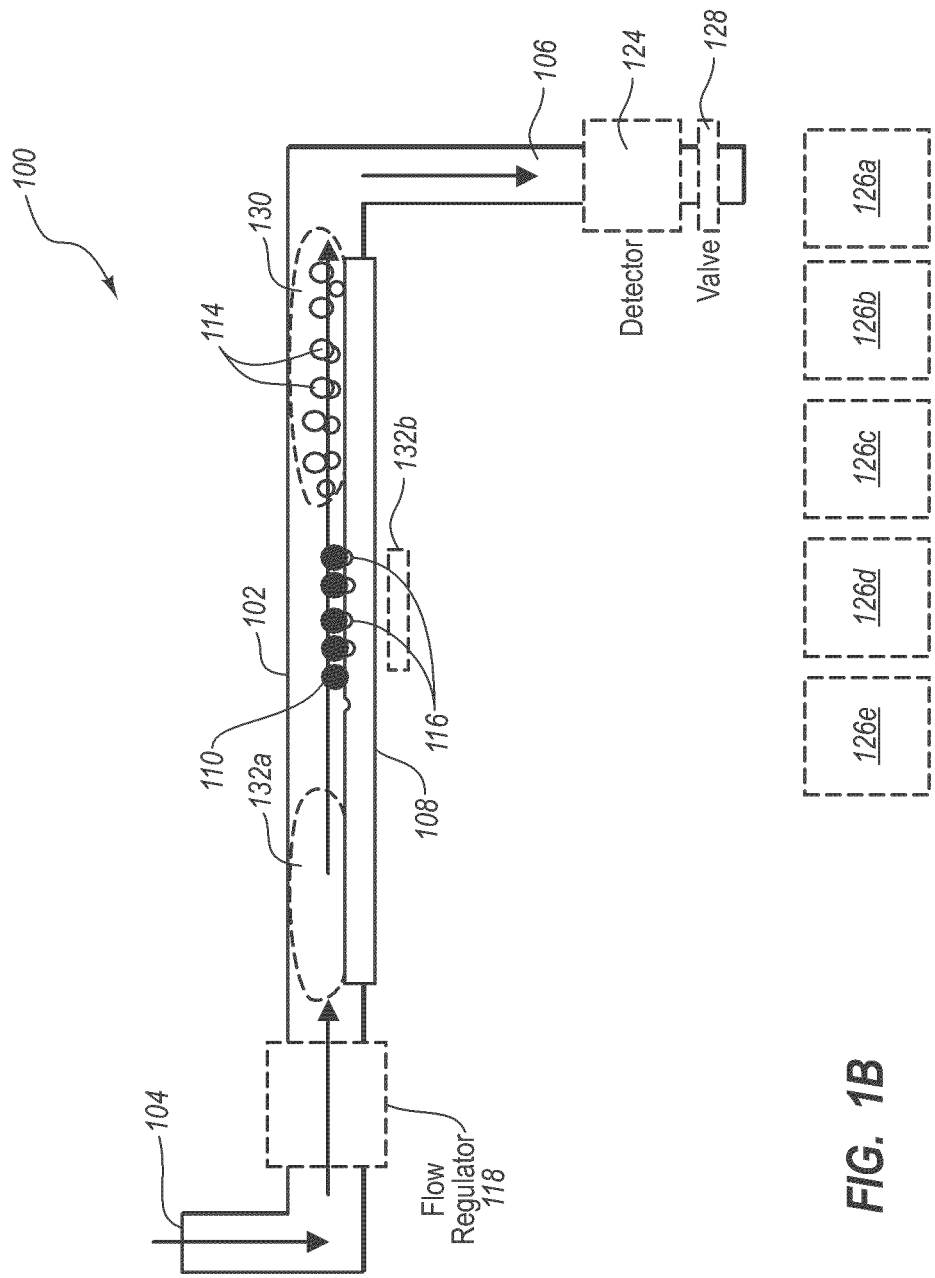
FIG. 1B through 1C are schematic diagram of the illustrative embodiment of a cell separator of FIG. 1A, in various stages of operation.

Turning to FIG. 1B, when the initial carrier fluid (FIG. 1A) passes over the flow surface, the indentations 116 on the flow surface 108 capture target cells 110. This separates the target cells 110 from the initial carrier fluid, leaving extraneous carrier fluid 130 to flow to the outlet 106 of the channel 102. As shown in FIG. 1B, capturing the target cells 110 creates a time difference between when the extraneous carrier fluid 130 and the captured target cells 110 arrive at the outlet 106. The extraneous carrier fluid 130 thus arrives at the outlet 106 before the target cells 110.

FIG. 1B also shows that when the initial carrier fluid (FIG. 1A) includes non-target cells 114 along with target cells 110, the non-target cells 114 pass over the flow surface 102, are not captured by the indentations 116, and flow to the outlet 106 along with the extraneous carrier fluid 130. This allows non-target cells 114 to be collected separately from the target cells 110.

After the target cells 110 are captured by the indentations 116, an energy source 132a and/or 132b are applied to the flow surface 108 at a particular time that triggers release of the target cells 110. The indentations 116 are responsive to the energy source 132a and/or 132b to allow the released target cells to flow to the outlet of the channel. The energy source 132a and/or 132b may also assist the released target cells 110 to flow to the outlet 106 of the channel 102. As shown in FIG. 1B, the target cells 110 flow at a delayed period after the extraneous carrier fluid 130 and/or non-target cells 114 flow to the outlet 106 of the channel 102.

In one embodiment, the energy source 132a is a discharge fluid that provides a fluid pressure to dislodge the captured target cells 110 from the indentations 116. In one embodiment, the flow rate of the discharge fluid is about 0.75 µL/min to about 25 µL/min, or about 5 µL/min to about 100 µL/min, about 15 µL/min to about 500 µL/min, as illustrative examples. The velocity of the discharge fluid is about 50 µm/s to about 400 µm/s, or about 100 µm/s to about 800 µm/s, as illustrative examples. The pressure of the discharge fluid is about 0.1 mPa to about 1 mPa, or about 0.1 mPa to about 0.8 mPa, or about 0.1 mPa to about 0.5 mPa, as illustrative examples. In one embodiment, the shear stress of the discharge fluid can be about $2.5 \times 10^{-3}$ dyn/cm² to about $6 \times 10^{-2}$ dyn/cm², or about $3.5 \times 10^{-3}$ dyn/cm², as illustrative examples.

In one embodiment, the discharge fluid 132a may be applied as a pulse of fluid having enough pressure to dislodge the captured target cells 110. In one embodiment, the fluid pressure is sufficient to overcome functional group interactions between the target cells 110 and the indentations 116. The amount of fluid pressure is such that the shear stress will be below a level at which target cells 110 contained in the indentations 116 would be damaged, and may vary depending on the type of target cell 110. Note that even though the figures show only initial and extraneous carrier fluids 112, 130 and discharge fluid 132a, the channel 102 may actually be continuously flowing a minimal amount of carrier fluid or other fluid so that the target cells 110 continue to thrive even when they are captured by the indentations 116. The continuous flow of a minimal amount of carrier fluid or other fluid has a fluid pressure that is sufficiently low enough not to dislodge the captured target cells 110.

In another embodiment, the energy source 132b is a stimulus that initiates a photo-chemical response in the indentations 116 to release the captured target cells 110, as will be described further below. The stimulus serves to make the indentations 116 less accessible to capture target cells 110, thus facilitating release of the target cells 110 to flow to outlet 106 of channel 102.

Figure 1C:
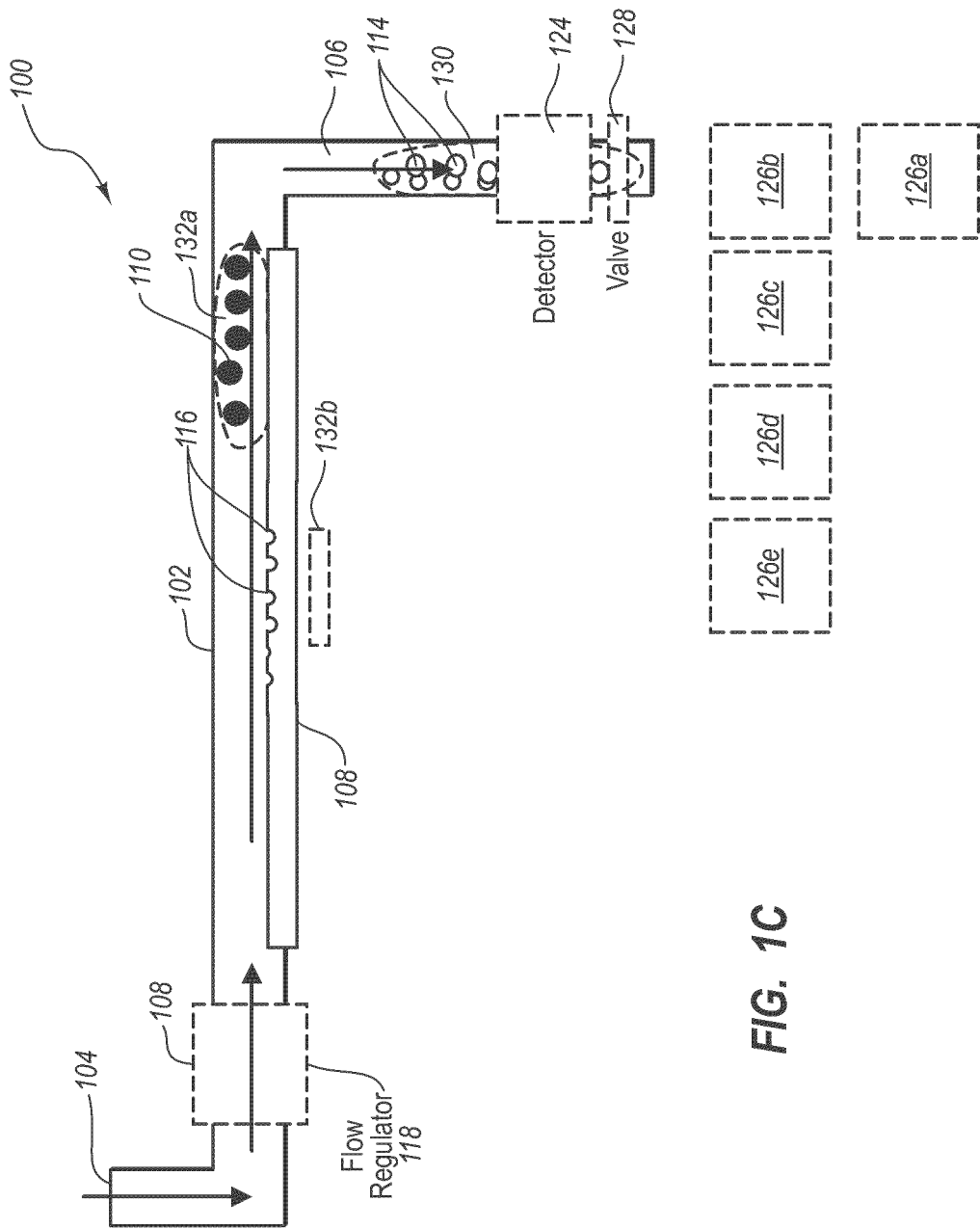

FIG. 1C shows the captured target cells 110 being released from the indentations 116 and allowed to flow to the outlet 106 of the channel 102. In embodiments where the first energy source is discharge fluid 132a, the discharge fluid 132a can then carry the released target cells 110 to the outlet 106 of the channel 102. Further, even in embodiments where the first energy source is a stimulus 132b, discharge fluid 132a may still be flowed through channel 102 to assist in moving the target cells 110 toward the outlet 106 of the channel 102.

The detector 124 can detect when the extraneous carrier fluid 130 and/or non-target cells 114 reach the outlet 106. In one embodiment, a plurality of sample containers 126a through 126e are positioned ready to collect discharge from the outlet 106. In one embodiment, the plurality of sample containers 126a through 126e are located on a revolving track (not shown). When the detector 124 detects the extraneous carrier fluid 130, the revolving track can begin to operate so that at least one sample container 126a through 126e is positioned under the outlet 106 to collect the extraneous carrier fluid 130. For example, FIG. 1C shows sample container 126b positioned to collect the extraneous carrier fluid 130 and/or non-target cells 114.

Figure 1D:
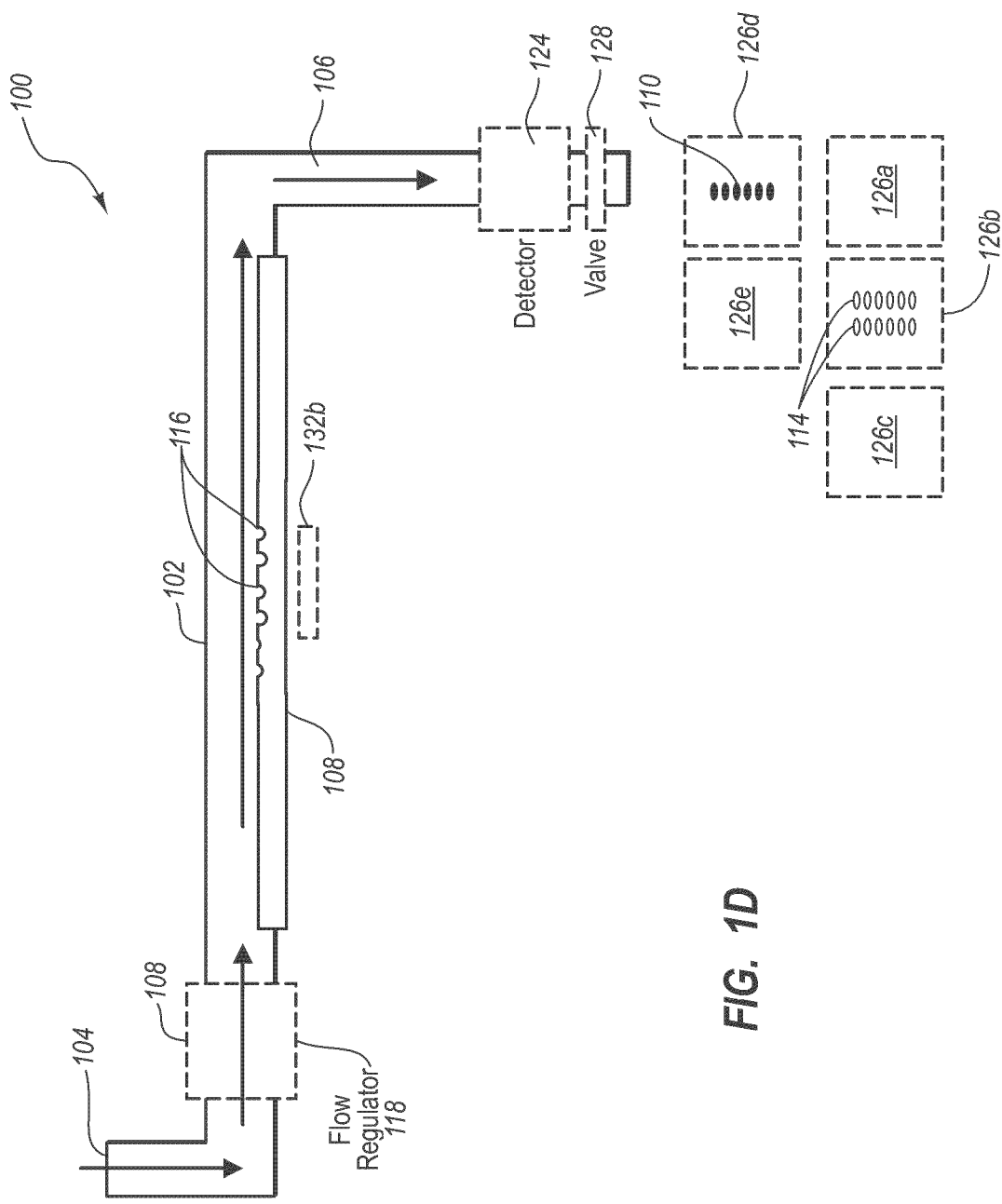

Likewise, the detector 124 can detect when the target cells 110 and/or discharge fluid 132a reach the outlet 106. FIG. 1D shows that when the detector 124 detects the target cells 110, the revolving track can operate so that a different sampling container 126d is positioned under the outlet 106 to collect target cells 110 and/or discharge fluid 132a.

The foregoing shows that the target cells 110 can thus be captured and retained by the indentations 116 of the flow surface 108 to delay the flow of target cells 110, thus separating the target cells 110 from the extraneous carrier fluid 130. As used herein, the term "extraneous carrier fluid" generally means the initial carrier fluid 112 less whatever was captured by the indentations 116. It is possible that the extraneous carrier fluid 130 includes at least some target cells 110 that were not captured by the indentations 116. In addition, it is possible that one or more non-target cells 114 were captured by one or more indentations 116, especially where a non-target cell 114 may have a portion having a smaller diameter than the diameter of the indentations 116. In these embodiments, the separation of the target cells 110 from the extraneous carrier fluid 130 should be viewed as increasing a concentration of the target cells 110 in a resulting collection sample. Or, the separation of the target cells 110 from the extraneous carrier fluid can be one step to increasing the purity of the target cells 110 in a resulting sample, where an additional step will be applied (such as another pass through the cell separator apparatus disclosed herein, filtration, centrifugation, antibody process, beads), to remove the remaining non-target cells 114.

FIG. 1E is an illustrative method for separating target cells using, for example, a cell separator. At 150, the method includes passing an initial carrier fluid containing target cells through an inlet of a channel to pass over a flow surface of the channel. The flow surface has indentations sized with a diameter that substantially matches a diameter of the target cells. At 152, the indentations on the flow surface capture target cells as the initial carrier fluid passes over the flow surface, leaving extraneous carrier fluid to flow to the outlet of the channel.

At 154, a first energy source is applied to initiate release of the captured target cells from the indentations such that the released target cells flow to the outlet of the channel. In one embodiment, the first energy source is applied at a particular time that causes the released target cells to flow to the outlet of the channel at a delayed period after the extraneous carrier fluid flows to the outlet of the channel. In one embodiment, the first energy source is a discharge fluid being applied to the inlet of the channel. In another embodiment, the first energy source is a stimuli, such as an optical device, being applied to the flow surface.

At 156, the extraneous carrier fluid is collected. At 158, the target cells are collected separately from the extraneous carrier fluid.

Forming Flow Surfaces Having Indentations

Figure 2A:
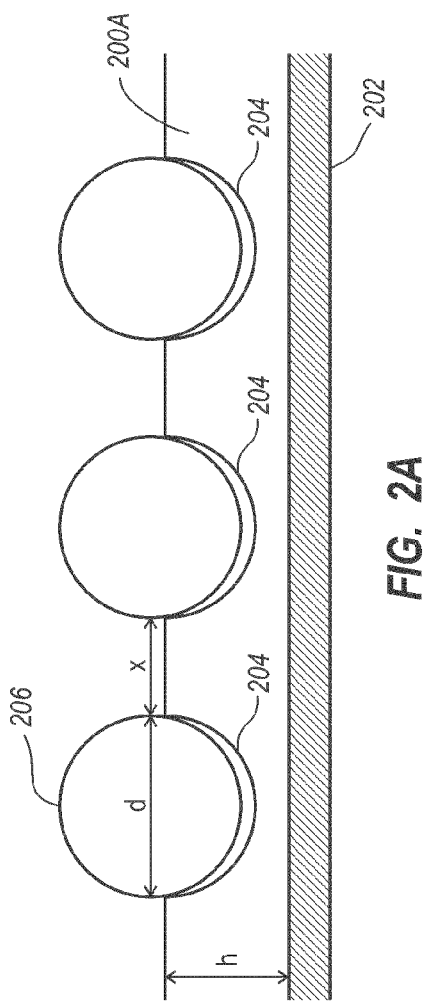
FIG. 2A through 2E are schematic diagrams of illustrative embodiments of flow surfaces having indentations and/or materials to form flow surfaces having indentations.
Figure 2B:
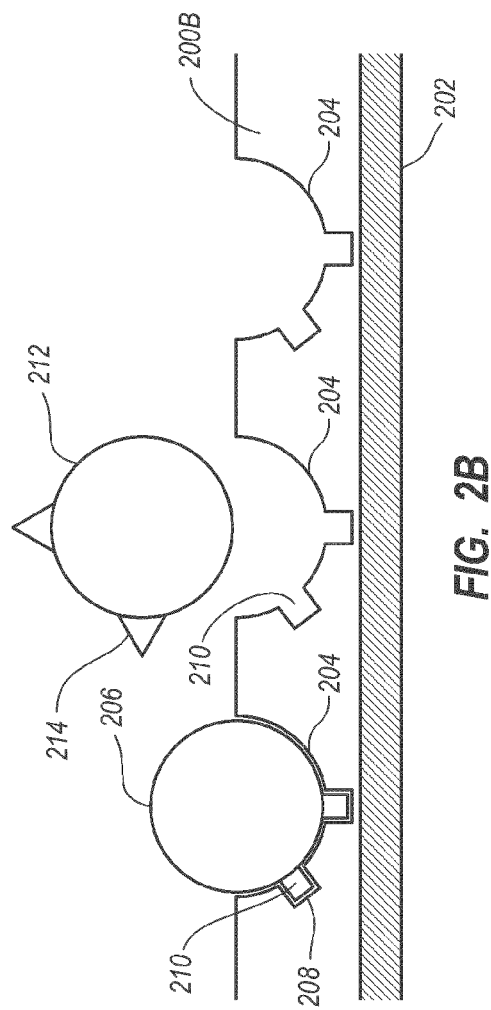
Figure 2C:
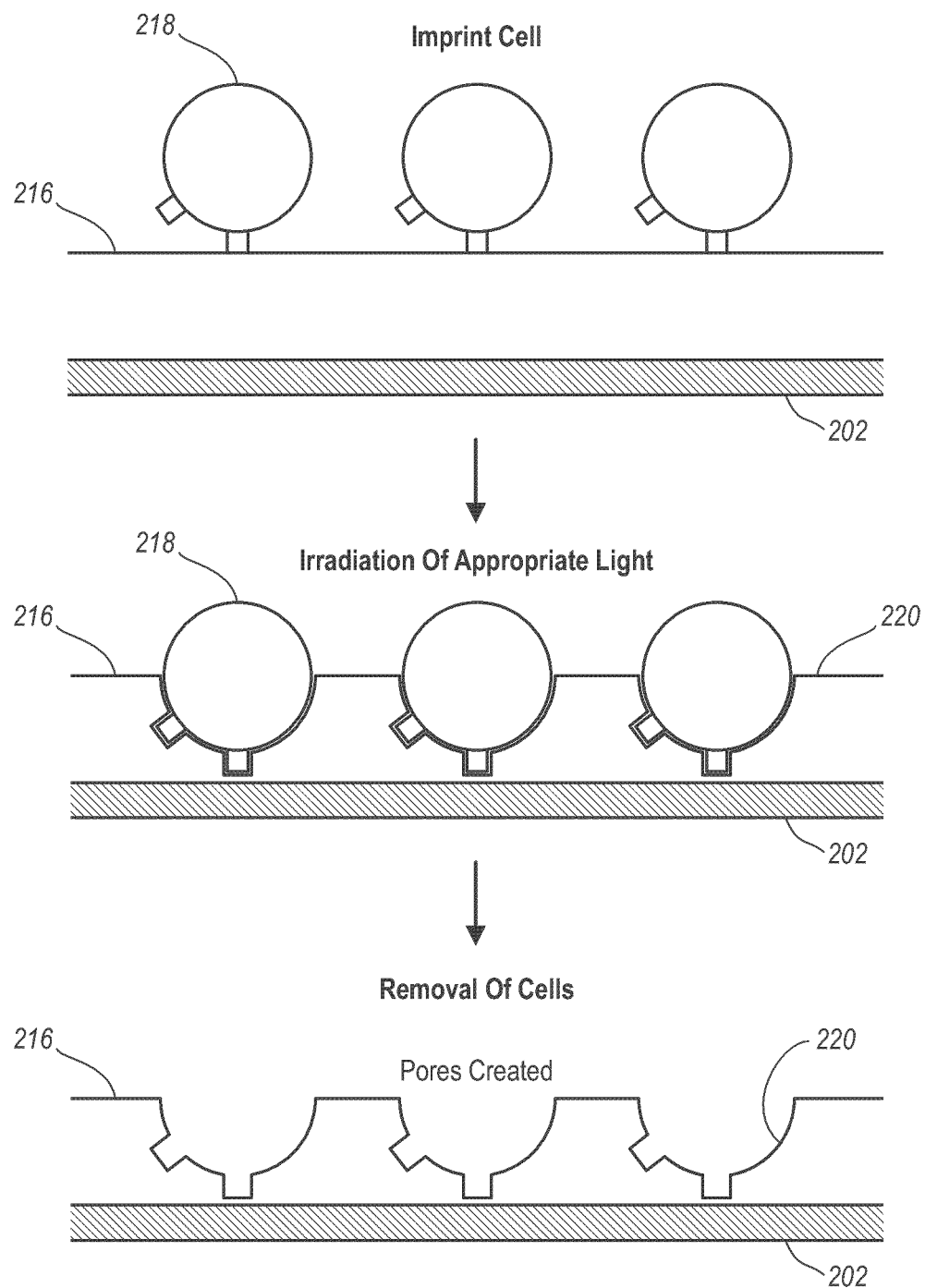

FIGS. 2A through 2C show various illustrative embodiments of flow surfaces, and particularly illustrative embodiments of indentations, that can be used for the targeted separation of cultured cells disclosed herein.

FIG. 2A shows one embodiment of a portion of a flow surface 200A located on a portion of a channel wall 202. The channel wall 202 serves as a substrate for the flow surface 200A. The materials of the channel wall 202 can be, but are not limited to, glass, quartz, polycarbonate, plastic, silicon, aluminum, stainless steel, ceramic, and the like. Other materials for the channel wall 202 will be readily apparent to those skilled in the art, thus further description will not be provided to avoid obscuring the concepts herein.

The flow surface 200A includes a plurality of indentations 204. Each indentation 204 is sized to receive at least a portion of a target cell 206. In one embodiment, the indentations 204 are rounded such that they conform to at least a portion of the target cell 206. In another embodiment, the indentations 204 may be cubical, triangular, or other polygonal three-dimensional shape. The height, h, of each indentation can be about 50 nm to about 500 µm, or about 500 nm to about 50 µm, or about 1000 nm to about 25 µm, as illustrative examples. The diameter, d, of each indentation can be about 50 nm to about 500 µm, or about 500 nm to about 50 µm, or about 1000 nm to about 25 µm, as illustrative examples.

In one embodiment, the indentations 204 are arranged in a plurality of rows to form an array of indentations. As shown in FIG. 2A, each row can have a distance, x, between indentations of about 10 nm to about 500 µm, or about 100 nm to about 50 µm, or about 200 nm to about 25 µm, as illustrative examples. In one embodiment, the rows of indentations align with the indentations the other rows. In another embodiment, the rows of indentations are offset from the indentations from adjacent rows. In one embodiment, the flow surface 200A includes an array of about 10 to about 1000 indentations by about 10,000 to about 1,000,000 indentations. Other embodiments of arranging an array of indentations are possible within the scope of this disclosure.

In one embodiment, the indentations 204 capture the target cells 206 using a physical interaction based on the indentations 204 having a diameter that is substantially similar to but not smaller than a diameter of a portion of the target cell 206. Various methods are possible for manufacturing indentations having these characteristics.

In one embodiment, inclined UV lithography can be used to form a pattern of indentations in a layer of spin-coated negative photo resist, such as SU-8, such as using methods taught in *Simple Fabrication Process for Single Cell Analysis chip composed of Embedded Microchannels and Orifices*, T. Suzuki et al., The 2nd International Symposium on Micro & Nano Technology (ISMNT-2), Hsinchu, Taiwan, pp. 222-225, which is incorporated herein by reference.

In one embodiment, a mold can be fabricated using negative photoresists (such as SU-8 50 and SU-8 2002). The mold has a desired number and size of protrusions that match the desired number and size of indentations desired of the flow surface. A layer of poly-dimethylsiloxane (PDMS) can be poured onto the mold, cured, then separated from the mold to provide a layer of PDMS layer having a pattern of indentations formed therein. Additional details regarding this method are found in *Dynamic Single Cell Culture Array*, Di Carlo et al. Lab Chip, 2006, 6, 1445-1449, which is incorporated herein by reference.

In another embodiment, capillary force lithography can be used to form indentations in a poly(ethylene glycol) dimethacrylate (PEG-DMA) film layered on a silicone/glass substrate. A PDMS stamp or mold contains protrusions and is laid on the PEG-DMA film, which forms indentations in the PEG-DMA film and exposes the substrate. The exposed substrate in the indentations can promote cell adsorption. Additional details regarding this method are found in *A Simple Soft Lithographic Route to Fabrication of Poly(Ethylene Glycol) Microstructures for Protein and Cell Patterning*, Suh et al., Biomaterials 25 (2004) 557-563, which is incorporated herein by reference.

In still another embodiment, indentations can be formed on a surface of photo-responsive polymer (such as an azobenzene-functionalized polyurethane film) using an optical near field generated around polystyrene spheres that have substantially the same diameter as the desired diameter of the indentation. The polystyrene spheres can be laid on a film of polyurethane polymer and irradiated with a linearly polarized $Ar^+$ laser at 488 nm. Without being tied to one theory, it is believed that the indentations form by a process of self-assembly resulting from interactions (e.g., dipole-dipole and/or hydrogen bonding) between the polystyrene spheres and the photo-responsive polymer. The polystyrene spheres can then be removed by washing them from the polyurethane polymer, leaving an array of indentations. A description of how the optical near field conforms azobenzene moieties from a cis to a trans state to cause the polyurethane to conform to the shape of the sphere is found in *Topographical Nanostructure Patterning on the Surface of a Thin Film of Polyurethane Containing Azobenzene Moiety Using the Optical Near Field around Polystyrene Spheres*, Hasegawa et al., Macromolecules, 2001, 34 (21), 7471-7476, which is incorporated herein by reference.

Thus far, methods for forming the flow surface with indentations have provided embodiments of indentations that capture the target cells using mechanical size-matching principles. In another embodiment, the indentations 204 also use chemical interactions to capture and retain target cells 206. In one embodiment, the indentations 204 have functional groups that interact with particular functional groups located on the target cells 206. Thus, target cells 206 can be selected based on whether they contain one or more functional groups that can interact with the functional groups of the indentations 204.

FIG. 2B shows an illustrative example of indentations having functional groups. FIG. 2B shows another illustrative example of a flow surface 200B bonded to channel wall 202. The flow surface 200B includes indentations 204 that include one or more functional groups 208 configured to interact with one or more functional groups 210 of the target cell 206. When a non-target target cell 206 has too large of a diameter and/or does not have functional groups complementary to the functional groups 208 of the indentations 104 (or may have one or more functional groups 214 that cannot interact with the functional groups 208 of the indentation 204), then the indentation 204 is not able to capture the non-target target cell 206. Note that the functional groups 214 and functional groups 210 are schematically representations of chemical functional groups only. The schematic shapes simply represent that the functional groups 214 and functional groups 210 are configured to be complementary to each other.

The functional groups 208 of indentations 204 may be generated as part of the process of making indentations 204, such as by using a polymer materials as the flow surface 200B that already has the desired functional groups 208.

In yet another embodiment, the surface of the indentations 204 may be imprinted complementarily with the target cells 206. This can include using the target cells 206 to actually form the indentations 204 (including forming functional groups 208) in a flow surface 200B. Thus, the flow surface 200B can be specialized to recognize certain target cells 206 due to imprinting. Even when non-target target cell 206 of the same or smaller size are contained in the initial carrier fluid, the indentations 204 do not capture the non-target target cell 206 because the functional groups 208 of the indentations 204 do not interact with the non-target cells 114.

Figure 2D:
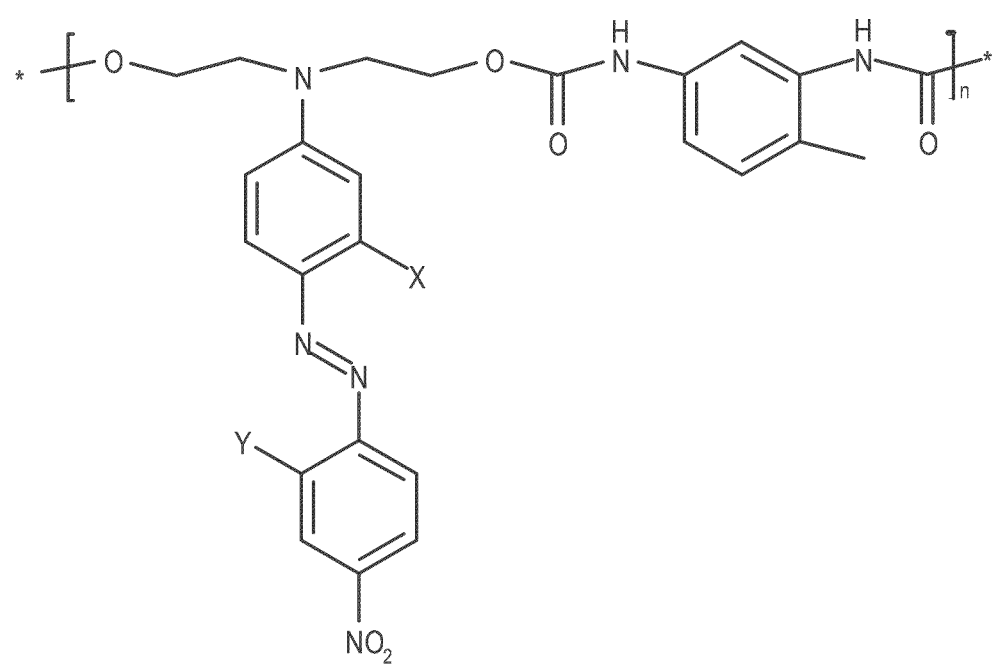

In one embodiment, a method for forming indentations 204 having functional groups 208 is shown in FIG. 2C. The substrate 202 is at least partially coated with a photo-responsive polymer 216. In one embodiment, the photo-responsive polymer 216 is a diazo compound, such as the diazo compound shown in FIG. 2D, which can be synthesized according to Watanabe et al., Chem., 1996, 6, 1487, incorporated herein by reference. The photo-responsive polymer film 216 can be formed by preparing a 8 wt % pyridine solutions of photo-responsive polymer. This solution is passed through a 0.20 mm filter (Millipore) to remove impurities before spin-coating. An optically clear film of photo-responsive polymer 216 is then spin-coated onto a substrate 202 (e.g., glass substrate). The resultant photo-responsive polymer film 216 is placed in a vacuum oven at 130° C. for over 24 hrs to remove any solvent.

To form the indentations, an aqueous solution of imprinting cells 218 held in saline, PBS, or other culture medium, is poured onto the photo-responsive polymer film 216. The imprinting cells 218 were allowed to arrange themselves on the photo-responsive polymer film 216 by a self-organization process. In one embodiment, the imprinting cells 218 contain the same functional groups 210 as the target cells. In one embodiment, the imprint cells 218 are the same type of cell as the target cells. The functional groups 210 assist to imprint a specific recognition site 208 into the indentation.

An optical device irradiates light onto the photo-responsive polymer film 216. Various light sources may be used, such as, but not limited to, a mercury-vapor lamp, a xenon-mercury lamp, a high intensity discharge lamp, an LED lamp, a laser (e.g., an argon laser, and the like. The light source can be radiated at normal incidence to the surface of the photo-responsive polymer film 216. The photo-responsive polymer film 216 can also be held vertically to avoid the effects of gravity. The range of wavelength from the optical device can be from about 400 nm to about 550 nm, from about 480 nm to about 490 nm, or about 488 nm, as illustrative examples. The irradiation time may range from 30 seconds to 10 minutes, or about 1 minute to about 5 minutes, or about 5 minutes, as illustrative examples. The intensity of the irradiation may range from about 70 W/cm2 to about 280 W/cm2.

Resultant distribution of intensity of the light irradiated on the imprinting cells 218 and on the photo-responsive polymer film creates indentations beneath the imprinting cells 218 due to a volume change between bright parts and dark parts of the photo-responsive polymer film similar to that taught in Hasegawa et al., Macromolecules, 34, 7471 (2001)), incorporated by reference. In other words, the imprinting cells 218 block the irradiation to create shade, which creates concaves in the photo-responsive polymer film. Without being tied to one theory, it is believed that the indentations form by a process of self-assembly resulting from interactions (e.g., dipole-dipole and/or hydrogen bonding) between the polystyrene spheres and the photo-responsive polymer.

The photo-responsive polymer film 216 was then washed with benzene for 3 days in order to remove the imprinting cells 218 from photo-responsive polymer 216 to reveal the indentations 220 formed therein. The photo-responsive polymer film 216 having indentations 220 was then subsequently dried in vacuo at 25° C. for 2 days.

Figure 2E:
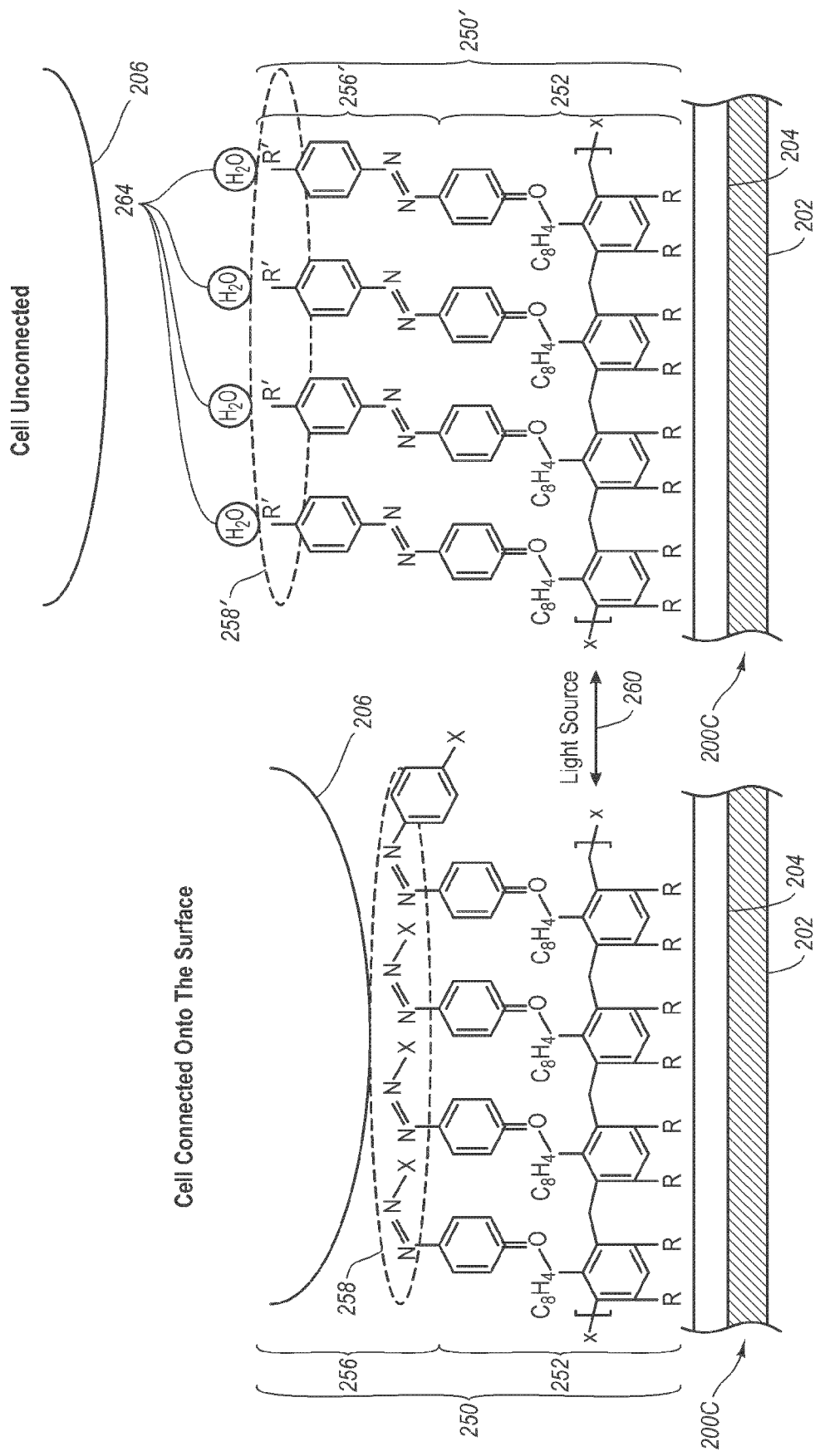

In still another embodiment, FIG. 2E shows another embodiment of a flow surface 200C in which at least a portion of a surface of the indentations 204 can be coated with a support molecule. FIG. 2E shows a schematic of an illustrative support molecule, a chemical operation of the support molecule upon irradiation by an optical energy source, and an interaction between a cell and the support molecule when the polarity of the support molecule changes. The support molecules 250 shown on the left has a first region 252 configured to bind to a surface of the indentation 204 and a photo-responsive region 256 on the opposing end of the first region 252. The support molecule 250' on the left is shown in a first conformation. The support molecule 250' on the right has a first region 252 bound to the indentation 204, but a photo-responsive region 256' in a second conformation due to a first optical energy source 260 irradiating the support molecule 250. The numerals for support molecule 250 and support molecule 250' are used to indicate that the conformation of the support molecule has changed.

The photo-responsive region 256 is configured to change conformation between at least a first polarization 258 (indicated by the dashed area on the left) and a second polarization 258' (indicated by the dashed area on the right) upon irradiation from at least the first optical energy source 260. The photo-responsive region 256/256' includes one or more polar groups that alter polarity from the first polarization 258 to the second polarization 258', and vice versa. In some embodiments, the support molecule may have additional functional groups that have other functionalities.

When the photo-responsive region 256 has the first polarization 258, the photo-responsive region 256 has a first conformation that is accessible to and/or capable of adhering to target cells 206. This is shown in FIG. 2E on the left by a cell 206 that is adhered to the photo-responsive region 256 having the first conformation. When the photo-responsive region 256' has the second conformation, the photo-responsive region 256' is more hydrophilic than the first polarization 256, making the photo-responsive region less accessible and/or less conducive to adhering to target cells 206. This is shown in FIG. 2E on the right by the photo-responsive region 256' being more likely to bond to water molecules 264 and less likely to adhere to cells so that the target cell 206 being unadhered, detached, or disconnected from the photo-responsive region 256' having the second polarization 258'.

Embodiments herein contemplate that when the photo-responsive region 256 of the support molecules is in the first conformation that is able to adhere to target cell 206, the first polarization 258 is more hydrophobic than the second polarization 258', thus encouraging cells to adhere thereto. When the photo-responsive region 256' conforms to the second conformation, the second polarization 258' is more hydrophilic than the first polarization 258, thus being more attracted to water than to hydrophobic lipid cellular walls. It may be the case that the first polarization 258 is actually somewhat hydrophilic, in which case, the second polarization 258' can be characterized as more hydrophilic than the first polarization 258. In some embodiments, the photo-responsive region may go through more than two conformations, with each conformation having a different polarization, phases, or grades of polarization, with some grades being more hydrophobic and some grades being more hydrophilic.

It may be the case that the first conformational state is actually somewhat hydrophilic, in which case, the second conformational state can be characterized as more hydrophilic than the first polarization. In some embodiments, the photo-responsive region may go through more than two conformations, with each conformation having a different polarization or phases or grades of polarization, with some grades being more hydrophobic and some grades being more hydrophilic. The terms "hydrophobic" and "hydrophilic" are used broadly in conjunction with terms like "more" and "less" so that it is clear that the disclosure herein is not limited to the first conformational state being hydrophobic per se or the second conformational state being hydrophilic per se. Rather, the second conformational state is generally "more hydrophilic" than the first conformational state. Or in other terms, the second conformational state is generally "less hydrophobic" than the first conformational state.

The embodiment of FIG. 2E shows one example of altering polarity of the photo-responsive region 256/256' using a cis-to-trans transformation of the support molecule 250/250'. The support molecule 250/250' shown in FIG. 2E is reproduced below:

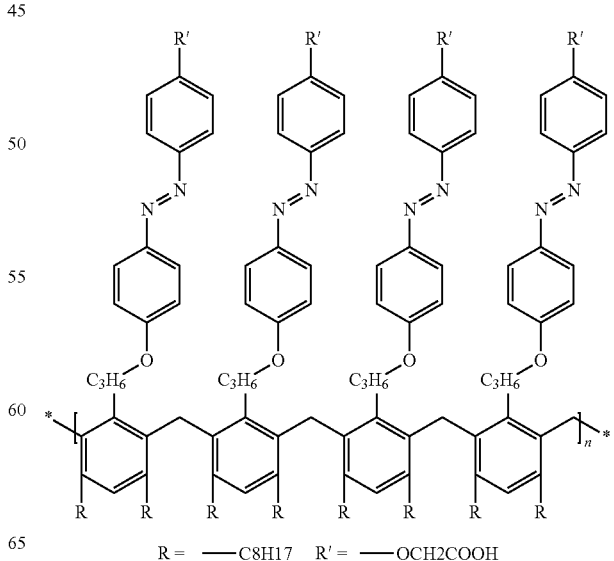

In one embodiment, R is $C_8H_{17}$ or $C_mH_{2m+1}$ where m is 3 to 18 and R' is $OCH_2COOH$, $OCH_2CH_2COOH$, $OCH_2CH_2OCH_2COOH$, or $OCH_2CH_2OCH_2CH_2COOH$. The diazo compound is a crown conformer of ocarboxymethylated calix[4]resorcinarene (CRA-CM) bearing four p-octylazobenzene residues at one of the rims of the cyclic skeleton. CRA-CM is a macrocyclic amphiphile (including the R group) forms the first region 252 that binds to the indentations 204. The azobenzene moieties (including the R' group) form the photo-responsive region 256/256'. The CRA-CM form a rigid cylindrical macrocycle that tethers the azobenzene moieties and can be densely packed into a single-molecule support layer.

The azobenzene moieties (i.e., the photo-responsive region 256/256') isomerizes upon irradiation of a certain wavelength of an optic energy source. The azobenzene moieties have polar groups R' that switch polarity from a first polarization 258 to a second polarization 258' upon irradiation by the optic energy source.

In one embodiment, the indentations 204 having support molecules 250 of an azobenzene compound may be prepared by immersing the flow surface 200C formed using any of the methods above in a dilute solution of CRA-CM, yielding a robust monolayer of support molecules 250 with dense packing over the flow surface and coating the indentations 204.

When the photo-responsive region 256' is more hydrophilic, the support molecules are more likely to bond to water molecules 264 than to the cells. This is also referred to as "wettability" of the indentations 204. This is due to a change in conformation of the photo-responsive region 256', which causes the photo-responsive region 256' to become less or more hydrophobic/hydrophilic depending on the conformation when manipulated by an optical energy source. When the photo-responsive region 256' is less hydrophilic, the photo-responsive region 256' is more able to adhere to cells. When the photo-responsive region 256' is more hydrophilic, the hydrophobic portions of the support molecules are less available and less susceptible to bonding with the membranes of the cultured cells and the hydrophilic portions of the photo-responsive region 256' is more likely to bond to water than to the cells. This wettability of the indentations 204 eases separation of the target cells 206 because the target cells 206 become naturally unadhered, detached, or disconnected to the indentation 204 in a noninvasive manner.

In some embodiments, a conformation of the photo-responsive region 256/256' not only affects the conformational state, but may also have a steric effect that contributes to cell adherence. When the photo-responsive region 256 is in the first conformation that is more conducive to cell adherence than the second conformation, the first conformation may also have a chemical structure that is more accessible to the cultured cells. This is shown in FIG. 2E by the diazo functional group N═N being located on top of the support molecule 250 and exposed to be accessible to a target cell 206. When the photo-responsive region 256' is in the second conformation, the photo-responsive region 256' may have a second chemical structure where sites to which the target cell 206 would normally adhere are now less accessible, making it less conducive for the target cell 206 to adhere. This is shown in FIG. 2E by the polar groups R' being on the top of the support molecule 250' and exposed to be accessible to water molecules 264, while the diazo functional group N═N is now part of the cyclic tethering chain. Further, the support molecules 250 are densely packed in a monolayer over the indentations 204 so the N═N diazo groups are surrounded by other cyclic chains, preventing access by target cell 206 to the diazo groups.

In one embodiment, the flow surface 200C and/or bottom of the channel wall 202 is at least partially transparent to allow light to pass through the bottom of the flow surface 200C. In another embodiment, the channel wall may have a top opening or be at least partially transparent allowing light to reach the flow surface 200C from above.

Turning back to FIGS. 1A through 1D, the support molecules 250 are operable in the indentations 116 to assist the capture and release of target cells 110. As shown in FIGS. 1A through 1D, the stimuli 132b may be an optical device that is operable to selectively radiate optical energy onto at least a portion of the flow surface 108 at the desired time. In one embodiment, the optic device irradiates a light in a wavelength of about 400 nm to about 500 nm, or about 420 nm to about 470 nm, or about 430 nm to about 440 nm, as illustrative examples. In one embodiment, the optic device irradiates a light having a power of about 1 $mW/cm^2$ to about 100,000 $mW/cm^2$, or about 10 $mW/cm^2$ to about 10,000 $mW/cm^2$, or about 100 $mW/cm^2$ to about 1,000 $mW/cm^2$, as illustrative examples. In one embodiment, the optic device 114 irradiates a light for about 0.1 sec to about 10,000 sec (2.75 days), or about 1 sec to about 1,000 sec (about 16 minutes), or about 10 sec to about 100 sec, as illustrative examples. In one embodiment, the optic device irradiates a light at a distance from the flow surface 108 of about 1 cm to about 200 cm, or about 5 cm to about 100 cm, or about 25 cm to about 50 cm, as illustrative examples. In each of these examples, the entire flow surface 108 does not have to be irradiated; rather an optic element can irradiate only a portion of the flow surface 108 at the wavelength, power, time period, and/or distance as illustratively described above. Further various combinations of wavelength, power, time period, and/or distance from the cell separator may be applied to trigger the photo-responsive region to conform from the first polarization to the second polarization.

In some embodiments, the photo-responsive region is activated using an optic device including, but not limited to, a mercury-vapor lamp, a xenon-mercury lamp, a high intensity discharge lamp, an LED lamp, and the like. Various optic devices are commercially sold and can be readily adapted to be included in an apparatus of this disclosure.

The foregoing provides efficient, cost-effective ways of separating and/or concentrating target cells from a carrier fluid that may have other non-target cells. While single target cells have been shown in the above illustrative embodiments, the term "target cell" also contemplates cell aggregations in which it is desired to separate and/or concentrate cell aggregations. Cells such as stem cells typically aggregate in a cell culture. Indentations can be created with an appropriate size of the aggregation based on the disclosure herein. Other variations will also be apparent based on the disclosure herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An apparatus for cell separation, the apparatus comprising:
    a channel having an inlet and an outlet, the inlet configured to receive an initial carrier fluid containing at least a first cell;
    a flow surface extending between the inlet and the outlet of the channel, wherein the flow surface includes a patterned surface that includes one or more indentations fabricated to exhibit at least one characteristic of the first cell, wherein the patterned surface is configured to selectively capture at least the first cell and to permit the carrier fluid to flow therethrough, and wherein the patterned surface of the flow surface is at least partially coated with one or more photo-responsive azobenzene compound molecules having a first region configured to bind to a surface of the flow surface and having a second photo-responsive region configured to change conformation between a first more hydrophobic conformation and a second more hydrophilic conformation responsive to irradiation from an optical energy source,
        wherein the first more hydrophobic conformation displays a diazo functional group (N=N) on a first exposed surface of the one or more photo-responsive azobenzene compound molecules allowing the at least one indentation to receive and interact with the first cell, and
        wherein the second more hydrophilic conformation displays a polar group on a second exposed surface of the one or more photo-responsive azobenzene compound molecules permitting release of the first cell from the at least one indentation; and
    a detector positioned downstream from and in fluid communication with the outlet of the channel, the detector configured to detect flow of one or more target cells flowing from the outlet of the channel.

2. The apparatus as recited in claim 1, wherein the one or more indentations are sized with a diameter substantially similar to a diameter of at least a portion of the first cell, wherein the one or more indentations are configured to capture one or more target cells from the initial carrier fluid and release captured one or more target cells responsive to an energy source to allow the released one or more target cells to flow to the outlet of the channel.

3. The apparatus as recited in claim 1, wherein the detector in fluid communication with the outlet of the channel is further configured to detect flow of extraneous carrier fluid flowing from the outlet of the channel.

4. The apparatus as recited in claim 3, wherein the initial carrier fluid includes one or more non-target cells that are not captured by the one or more indentations when passing over the flow surface.

5. The apparatus as recited in claim 1, wherein the one or more first cells are osteocytes, epidermal cells, organ cells, epithelial cells, ciliated epithelial cell, chondrocytes osteoblasts, osteocytes, muscle cells, glia cells, schwan cells, myelin sheath cells, hematopoietic cells, mast cells, hepatocytes, hepatic parenchymal cells, bone marrow cells, embryonic stem cells (ESCs), pluripotent stem cells, induced pluripotent stem cells, embryonic stem cells, adult stem cells, or multipotent and induced multipotent stem cells, blood cells.

6. The apparatus as recited in claim 1, wherein the initial carrier fluid contains at least a second non-target cell selected from the group consisting of feeder cells, stimulating cells, immune cells, and combinations thereof.

7. The apparatus as recited in claim 1, wherein the patterned surface of the flow surface comprises one or more of a negative photoresist, poly-dimethylsiloxane, poly(ethylene glycol) dimethacrylate, an azobenzene-functionalized polyurethane, or a combination thereof.

8. The apparatus as recited in claim 1, wherein the one or more photo-responsive azobenzene compound molecules have a formula of:

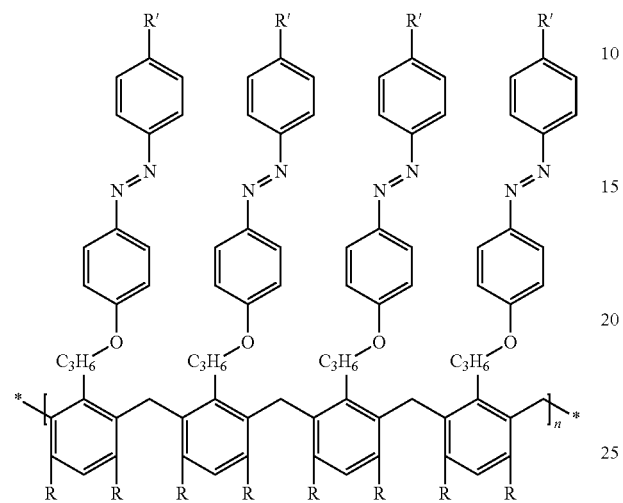

wherein R is $C_8H_{17}$ or $C_mH_{2m+1}$ where m is 3 to 18 and R' is $OCH_2COOH$, $OCH_2CH_2COOH$, $OCH_2CH_2OCH_2COOH$, or $OCH_2CH_2OCH_2CH_2COOH$.

9. The apparatus as recited in claim 1, further comprising an optical device configured to irradiate the photo-responsive region of at least some of the photo-responsive molecules with the optical energy source.

10. The apparatus as recited in claim 1, wherein the patterned surface is fabricated using one or more of photolithography, negative photoresist, capillary force lithography, patterning a photo-responsive polymer, and combinations thereof.

11. A method for separating target cells from a carrier fluid, the method comprising:
passing an initial carrier fluid containing a plurality of first target cells through an inlet of a channel to pass over a flow surface of the channel, wherein the flow surface includes a patterned surface having at least one indentation fabricated to exhibit at least one characteristic of the first cell, and wherein the at least one indentation is configured to selectively capture one or more of the plurality of first target cells as the initial carrier fluid passes over the flow surface, leaving extraneous carrier fluid to flow to an outlet of the channel; and
applying an optical energy source to initiate release of the captured one or more target cells from the at least one indentation such that the released one or more target cells flow to the outlet of the channel;
wherein the patterned surface of the flow surface is at least partially coated with one or more photo-responsive azobenzene compound molecules having a first region configured to bind to a surface of the flow surface and having a second photo-responsive region configured to change conformation between a first more hydrophobic conformation and a second more hydrophilic conformation responsive to irradiation from the optical energy source;
wherein the first more hydrophobic conformation displays a diazo functional group (N═N) on a first exposed surface of the one or more photo-responsive azobenzene compound molecules allowing the at least one indentation to receive and interact with the first cell; and
wherein the second more hydrophilic conformation displays a polar group on a second exposed surface of the one or more photo-responsive azobenzene compound molecules permitting release of the first cell from the at least one indentation.

12. The method as recited in claim 11, further comprising collecting the extraneous carrier fluid; and
collecting the at least one target cell separately from the extraneous carrier fluid.

13. The method as recited in claim 11, further comprising detecting when the extraneous carrier fluid has been collected so as to determine when to apply the energy source onto the flow surface.

14. The method as recited in claim 11, further comprising:
radiating an optical energy onto at least some of the one or more photo-responsive azobenzene compound molecules so that the photo-responsive region changes to the second conformation so that the at least one indentation releases the at least one target cell.

* * * * *

UNITED STATES PATENT AND TRADEMARK OFFICE
CERTIFICATE OF CORRECTION

PATENT NO. : 8,951,765 B2
APPLICATION NO. : 12/624972
DATED : February 10, 2015
INVENTOR(S) : Ueda It is certified that error appears in the above-identified patent and that said Letters Patent is hereby corrected as shown below:

In the Specification

In Column 2, Line 28, delete "FIG." and insert -- FIGS. --, therefor.

In Column 2, Line 31, delete "FIG." and insert -- FIGS. --, therefor.

In Column 3, Line 21, delete "schwan" and insert -- shwann --, therefor.

In Column 3, Line 27, delete "mesencymal" and insert -- mesenchymal --, therefor.

In Column 3, Lines 30-50, delete "Examples......................ture." and insert the same at Line 31, as a new paragraph.

In Column 3, Line 45, delete "archea" and insert -- archaea --, therefor.

In Column 4, Line 49, delete "adherance" and insert -- adherence --, therefor.

In Column 4, Line 53, delete "adherance" and insert -- adherence --, therefor.

In Column 7, Line 5, delete "electlomagnetic" and insert -- electromagnetic --, therefor.

In Column 7, Line 35, delete "Coutler." and insert -- Coulter. --, therefor.

In Column 7, Line 50, delete "102. When detector 102" and insert -- 124. When detector 124 --, therefor.

In Column 8, Line 8, delete "se." and insert -- serum. --, therefor.

In Column 8, Line 37, delete "102," and insert -- 108, --, therefor.

Signed and Sealed this
Eighth Day of September, 2015

Michelle K. Lee
*Director of the United States Patent and Trademark Office*

In Column 11, Line 30, delete "al." and insert -- al., --, therefor.

In Column 12, Line 18, delete "104" and insert -- 204 --, therefor.

In Column 13, Line 15, delete "W/cm2 to about 280 W/cm2." and insert -- $W/cm^2$ to about 280 $W/cm^2$. --, therefor.

In Column 14, Line 66, delete "R =  ——C8H17   R' = ——OCH2COOH" and insert -- R = ——$C_8H_{17}$   R' = ——$OCH_2COOH$ --, therefor.

In Column 16, Line 20, delete "device 114" and insert -- device --, therefor.

In Column 17, Line 49, delete "and or" and insert -- and/or --, therefor.

In the Claims

In Column 20, Line 56, in Claim 5, delete "schwan" and insert -- schwann --, therefor.